(12) United States Patent
Park

(10) Patent No.: US 9,084,806 B2
(45) Date of Patent: Jul. 21, 2015

(54) HYPOXIA-RESPONSIVE NANOPARTICLE FOR THERAPY AND IMAGING OF HYPOXIA-INVOLVING DISEASES

(71) Applicant: RESEARCH & BUSINESS FOUNDATION SUNGKYUNKWAN UNIVERSITY, Suwon-si (KR)

(72) Inventor: Jae Hyung Park, Suwon-si (KR)

(73) Assignee: Research & Business Foundation Sungkyunkwan University, Suwon-si (KR)

(*) Notice: Subject to any disclaimer, the term of this patent is extended or adjusted under 35 U.S.C. 154(b) by 17 days.

(21) Appl. No.: 14/078,075

(22) Filed: Nov. 12, 2013

(65) Prior Publication Data
US 2014/0141084 A1    May 22, 2014

(30) Foreign Application Priority Data
Nov. 12, 2012 (KR) .................. 10-2012-0127483

(51) Int. Cl.
| A61K 9/14 | (2006.01) |
| A61K 31/704 | (2006.01) |
| A61K 47/48 | (2006.01) |
| A61K 9/51 | (2006.01) |

(52) U.S. Cl.
CPC ......... *A61K 31/704* (2013.01); *A61K 47/48923* (2013.01); *A61K 9/5161* (2013.01); *Y10T 428/2982* (2015.01)

(58) Field of Classification Search
None
See application file for complete search history.

(56) References Cited

U.S. PATENT DOCUMENTS

| 2011/0150837 A1* | 6/2011 | Chan et al. ............. 424/85.7 |
| 2014/0010760 A1* | 1/2014 | Giri et al. ............... 424/9.6 |

FOREIGN PATENT DOCUMENTS

EP         0302416 A1 *  7/1988

* cited by examiner

*Primary Examiner* — Robert A Wax
*Assistant Examiner* — Melissa Mercier
(74) *Attorney, Agent, or Firm* — NSIP Law

(57) ABSTRACT

The present invention relates to an amphiphilic polymer whose property and structure can change under hypoxic conditions, and to nanoparticles formed by self-assembly of the amphiphilic polymer. The hypoxia-responsive nanoparticles according to the present invention release a drug selectively under hypoxic conditions. Thus, the nanoparticles can be used for the selective diagnosis and treatment for diseases that are accompanied by hypoxia. Particularly, the nanoparticles can release a drug only to a targeted tumor in cancer therapy, and thus have minimized side effects and maximized therapeutic effects.

16 Claims, 12 Drawing Sheets

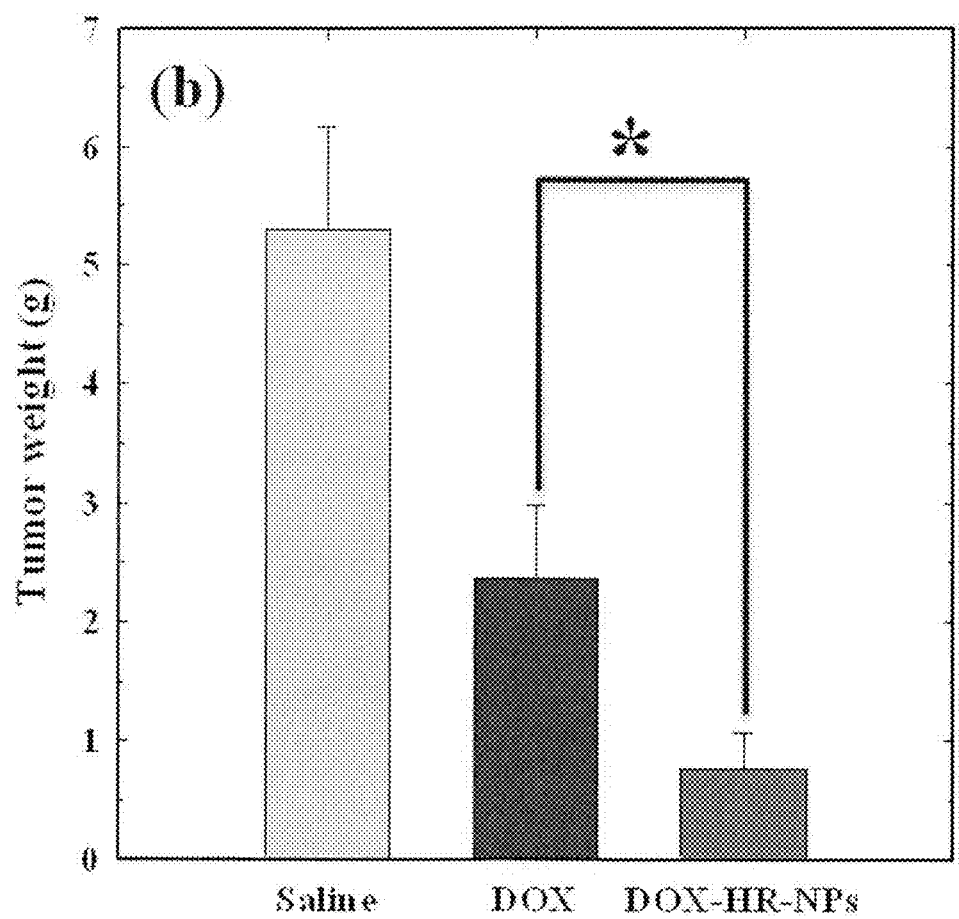

HYPOXIA-RESPONSIVE NANOPARTICLE FOR THERAPY AND IMAGING OF HYPOXIA-INVOLVING DISEASES

TECHNICAL FIELD

The present invention relates to nanoparticles that change their properties under hypoxic conditions, and thus can be used for the diagnosis and treatment of hypoxia-related diseases.

BACKGROUND ART

Hypoxia, a pathological condition deprived of adequate oxygen supply, is a hallmark of various intractable diseases such as cancer, cardiopathy, ischemia, rheumatoid arthritis, and vascular diseases. For example, experimental and clinical studies have demonstrated that tissue partial pressure of oxygen ($tPO_2$), measured in ischemic stroke and cancer, is near zero mm Hg which is substantially lower than that in the normal tissue (~30 mm Hg). Since hypoxia is involved in many aspects of the biology of diseases, it significantly affects the therapeutic responses to the diseases. In particular, hypoxia is a negative factor for cancer therapy because it contributes to chemoresistance, radioresistance, angiogenesis, invasiveness, and metastasis. Nevertheless, owing to its unique features which are rarely found in the normal tissue, hypoxia is emerging as the primary target for developments of diagnostic agents and therapeutic drugs. The representative approaches for hypoxia-targeted cancer therapy are based on regulation of hypoxia inducible factor-1 causing chemoresistance and on the use of the bioreductive prodrugs which can be activated in the reductive environment of hypoxia.

For hypoxia imaging, many nitroaromatic or quinone derivatives as the hypoxia-sensitive moieties have been employed for molecular design of diagnostic agents. Of the derivatives investigated, 2-nitroimidazoles have been most widely utilized for developments of imaging agents as well as the bioreductive prodrugs because of their high sensitivity to hypoxia. Under hypoxic conditions, 2-nitroimidazoles (NIs) are changed to the hydrophilic 2-aminoimidazole via a series of selective bioreductions, which are highly reactive to the macromolecules in hypoxic tissue.

Self-assembled polymeric nanoparticles, composed of amphiphilic polymers, have emerged as a promising nanocarrier for various anticancer drugs. They exhibit unique characteristics as drug carriers, including an enhancement of drug solubility, high thermodynamic stability, and preferential accumulation into the tumor tissue via the enhanced permeation and retention (EPR) effect. Conventional nanocarriers, however, often show limited antitumor efficacy because they release the drug in a sustained manner even at the target site of action. In recent years, to enhance therapeutic efficacy, polymeric materials which respond to the tumor pathophysiological conditions have been utilized to construct the nanoparticles for drug delivery. Such stimuli-responsive nanocarriers are expected to reach the tumor site via EPR effect and release the drug rapidly when they are exposed to the tumor tissue. To date, many stimuli have been explored for development of smart nanocarriers, including ultraviolet, glutathione, pH, and temperature. Consequently, a few of the stimuli-responsive drug carriers have been advanced to the clinical trial.

However, despite the fact that hypoxia is related to various intractable diseases, a polymer that actively responds hypoxic conditions to release a drug, and nanoparticles comprising the same, have not yet been developed.

DISCLOSURE

Technical Problem

Accordingly, the present inventors have conducted on nanocarriers that can be used for the diagnosis and treatment of various intractable diseases that are accompanied by hypoxia, and as a result, have found that an amphiphilic polymer conjugate whose structure changes according to oxygen concentration releases a drug selectively under hypoxic conditions, and thus can be used for the diagnosis and treatment of hypoxia-related diseases, thereby completing the present invention.

Technical Solution

The present invention provides an amphiphilic polymer wherein a compound of the following formula 1, which has an amine group, is conjugated by an amide bond to a carboxymethyl dextran (CM-Dex) having a carboxyl group:

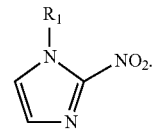

Formula 1 wherein $R_1$ is amine or a $C_1$-$C_{10}$ alkylamine.

In the present invention, the amphiphilic polymer may have a molecular weight of 5,000-1,000,000, but is not limited thereto.

The present invention also provides nanoparticles formed by self-assembly of the inventive amphiphilic polymer in an aqueous solvent, wherein the compound represented by formula 1 is located in the core of the nanoparticle, and the carboxymethyl dextran is located in the shell of the nanoparticle.

Hereinafter, the present invention will be described in detail.

As used herein, the term "hypoxia" refers to the case in which the oxygen partial pressure of tissue cells is abnormally low compared to that of normal tissue. It appears commonly in intractable diseases, including cancer, ischemic stroke, and arthritis. In the case of cancer, as cancer tissue grows, it encounters a hypoxic environment because the inside of solid cancer does not receive oxygen from blood vessels. For example, the partial pressure of oxygen in normal tissue is about 30 mmHg, whereas the oxygen partial pressure of cancer tissue approaches 0 mmHg.

The amphiphilic polymer of the present invention is characterized in that it exhibits hypoxia responsiveness in which the nitro group of the compound represented by formula 1 is reduced to an amino group under hypoxic conditions. Thus, the use of the amphiphilic polymer of the present invention can provide hypoxia-responsive nanoparticles and a drug delivery carrier.

In the moiety of the compound of formula 1 in the amphiphilic polymer, the nitro group (—$NO_2$) of 2-nitroimidazole can be reduced to an amino group (—$NH_2$) under a hypoxic condition (20 mmHg or lower, preferably about 0 mmHg) due to its selective reducing property so that the 2-nitroimidazole is converted to 2-aminoimidazole. Herein, because the amino group shows high hydrophilicity compared to the nitro group, the compound of formula 1 is reduced under hypoxic conditions, and thus becomes hydrophilic. Indeed, 2-aminoimidazole that is a reductive derivative of 2-nitroimidazole has the property of readily dissolving in water. This reduction of nitro to amine occurs via the transfer of six electrons, involving the nitroso (—N═O) and hydroxylamino (—NHOH) intermediates.

The compound of formula 1, which has an amine group, is an amine-modified 2-nitroimidazole compound that shows hydrophobicity. As used herein, the term "hydrophobicity" means the property of the compound that is self-assembled without being substantially dissolved in water or an aqueous phase due to repulsion with water. The compound represented by formula 1 contains a nitro group (—NO$_2$), a hydrophobic functional group, and thus can be completely hydrophobic.

Non-limiting examples of the compound represented by formula 1 include a compound (6-(2-nitro-1H-imidazol-1-yl)hexan-1-amine) represented by the following formula 2 wherein $R_1$ is a $C_6$ alkylamine:

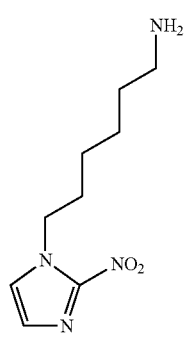

Formula 2

The compound represented by formula 2 can be prepared according to the following reaction scheme by reacting nitroimidazole with 6-(Boc-amino)hexyl bromide to produce 6-(2-nitroimidazole)hexylamine (step 1), concentrating the product obtained in step 1, dissolving the concentrate in methanol, and then adding HCl thereto (step 2).

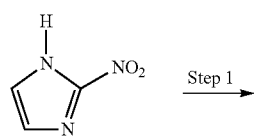

Step 1

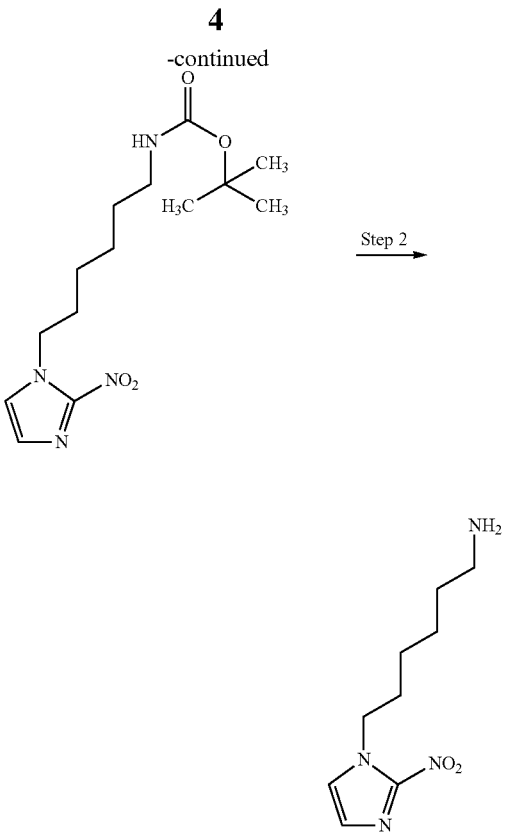

As used herein, the term "carboxymethyl dextran" refers to a kind of polysaccharide that may be represented by the following structural formula. The carboxymethyl dextran has biocompatibility and biodegradability, and thus has been widely used as a drug carrier.

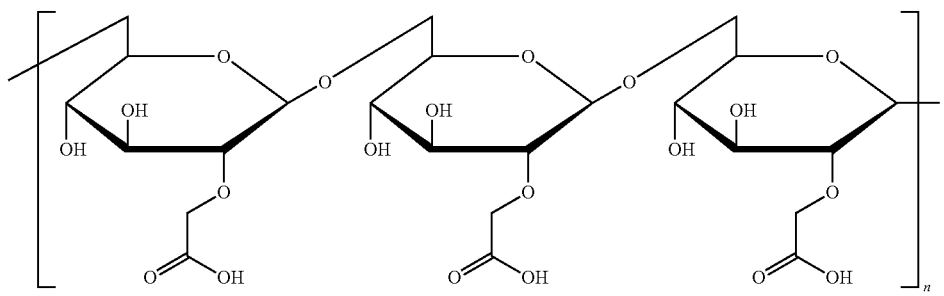

n of the structural formula of the carboxymethyl dextran may be 10 to 2,000, but is not limited thereto.

In the present invention, the carboxymethyl dextran forms a hydrophilic backbone, and the compound represented by formula 1 may be conjugated to the carboxymethyl dextran by an amide bond to impart hydrophobicity to the carboxymethyl dextran, thereby forming an amphiphilic polymer.

Specifically, the carboxymethyl dextran (CM-Dex) and the compound represented by formula 2 may be conjugated to each other according to the following reaction scheme to form an amphiphilic polymer:

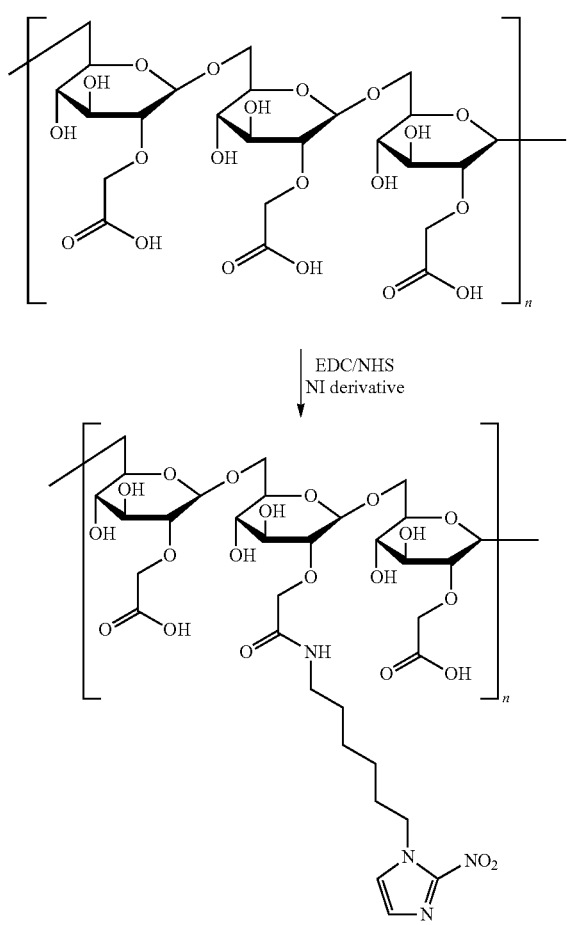

In the inventive conjugate of the carboxymethyl dextran and the compound of formula 1, 8-20 compounds represented by formula 1 may be conjugated per 100 carboxyl groups of the carboxymethyl dextran. Preferably, 8-11 compounds represented by formula 1 may be conjugated. If less than 8 compounds of formula 1 are conjugated, they cannot form nanoparticles in an aqueous phase due to excessively high hydrophilicity. If more than 20 compounds of formula 1 are conjugated, the size of the resulting particles will excessively increase, or these compounds will precipitate without forming nanoparticles in an aqueous phase.

Further, the present invention provides nanoparticles formed by self-assembly of the amphiphilic polymer in an aqueous solvent, wherein the compound represented by formula 1 is located in the core of the nanoparticles, and the carboxymethyl dextran is located in the shell of the nanoparticles.

The polymer according to the present invention shows amphiphilicity due to the hydrophobic group (2-nitroimidazole) introduced into the hydrophilic carboxymethyl dextran, and thus can be self-assembled in an aqueous solvent to form nanoparticles. Herein, the hydrophobic compound (2-nitroimidazole) of formula 1 is located in the core of the nanoparticle due to repulsion with water to form a hydrophobic core, and the hydrophilic carboxymethyl dextran is located in the shell of the nanoparticle. Particularly, hydrophobic additives (e.g., hydrophobic drug) may be encapsulated in the hydrophobic core of the nanoparticles.

In the present invention, the aqueous solvent may be water, a mixture thereof, or a buffer having a biological pH.

The size of the formed nanoparticles varies depending on the amount of compound of formula 1 conjugated per 100 carboxyl groups of the carboxymethyl dextran. Preferably, the produced nanoparticles may have an average diameter between 170 nm and 500 nm, and preferably 170 nm and 200 nm.

In the self-assembled nanoparticles, the hydrophilic moiety is located in the shell of the particles, and the hydrophobic moiety is located in the core of the particles. In the nanoparticles, the nitro group of the compound represented by formula 1 can be reduced to an amino group under an oxygen partial pressure of 20 mmHg or lower, which is a hypoxic condition. In other words, when the nitro group of the hydrophobic compound of formula 1 is exposed to a hypoxic environment, it is reduced to an amine group to become hydrophilic, as described above. Based on this property, the nanoparticles can be used for the diagnosis and treatment of hypoxia-related diseases.

The nanoparticles of the present invention may include additives such as a drug. The additives are preferably hydrophobic, because the core of the nanoparticles is hydrophobic, and in this case, hydrophobic additives (e.g., drug) can be encapsulated in the particles during self-assembly. The hydrophobic additives also include hydrophilic additives whose surface was hydrophobically modified. Particularly, in view of medical usefulness, the additives may be hydrophobic drugs, hydrophobic contrast agents, hydrophobically surface-modified drugs, hydrophobically surface-modified contrast agents, or combinations thereof.

Further, the nanoparticles of the present invention can be accumulated specifically in cancer tissue by the enhanced permeation and retention (EPR) effect. When a drug is delivered using the EPR effect, it does not depend on a targeted site specific to cancer cells, unlike a positive drug targeting system, and thus the drug can be delivered specifically to cancer cells even by oral or simple intravenous administration.

When the inventive nanoparticles including hydrophobic additives are exposed to a hypoxic environment (20 mmHg or lower) at a tumor location during their movement along blood vessels, the nitro group of the compound of formula 1 in the nanoparticle is reduced to an amine group. Thus, the core of the nanoparticles becomes hydrophilic, and the hydrophobic additives included in the core are released to the outside of the nanoparticles due to repulsion. In other words, the additives can be released selectively under a hypoxic environment.

Thus, the hypoxia-responsive nanoparticles of the present invention can be used as carriers for delivery of drugs for diagnosing and treating hypoxia-related diseases.

Non-limiting examples of hypoxia-related diseases include cancer, heart diseases, ischemic diseases, rheumatoid arthritis, and blood vessel-related diseases. Thus, the nanoparticles of the present invention can be used as carriers capable of delivering drugs related to the diagnosis and treatment of the above diseases to disease sites.

More specifically, additives that may be encapsulated in the nanoparticles may include any drug that can be encapsulated in the hydrophobic core of the nanoparticles composed of the amphiphilic polymer. Non-limiting examples of the additives include anticancer agents, including paclitaxel, doxorubicin, cis-platin, decetaxel, tamoxifen, camtothecin, anasterozole, carboplatin, topotecan, belotecan, irinotecan, gleevec, and vincristine. In addition, non-limiting examples of the hydrophobic drugs include anti-inflammatory agents, including salicylates, ibuprofen, naproxen, fenoprofen, indomethacin, phenyltazone, methotrexate, cyclophosphamide, mechlorethamine, dexamethasone, prednisolone, celecoxib, valdecoxib, nimesulide, cortisone, and corticosteroid.

In an example of the present invention, the present inventors confirmed live animal NIRF imaging demonstrated that nanoparticles of the present invention (HR-NPs) could effectively accumulate at the tumor site. As a consequence, DOX-HR-NPs exhibited enhanced antitumor efficacy, compared to free DOX. Overall, the results indicated that nanoparticles of the present invention are promising drug carriers for selective delivery of hydrophobic drugs into hypoxic cells.

Advantageous Effects

The hypoxia-responsive nanoparticles according to the present invention release a drug selectively under hypoxic conditions due to a change in their property. Thus, the nanoparticles of the present invention can be used for the selective diagnosis and treatment for diseases that are accompanied by hypoxia. Particularly, the nanoparticles of the present invention can release a drug only to a targeted tumor in cancer therapy, and thus have minimized side effects and maximized therapeutic effects.

MODE FOR INVENTION

Hereinafter, the present invention will be described in detail with reference to examples. It is to be understood, however, that these examples are for illustrative purposes only and are not intended to limit the scope of the present invention.

Example 1

Syntheses of Hypoxia-Responsive Conjugates (Nanoparticles)

1) Syntheses of NI Derivative

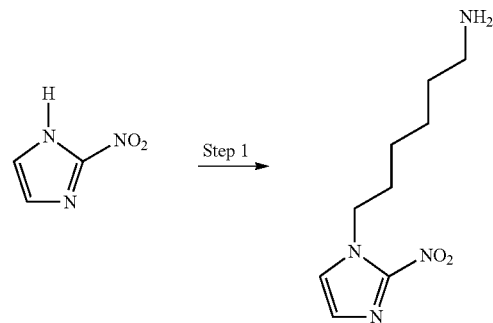 [SMILES: O=[N+]([O-])c1ncc[nH]1 ; NCCCCCCn1ccnc1[N+](=O)[O-]]

NI was converted to 6-(2-nitroimidazole)hexylamine for chemical reaction with the carboxylic acids of CM-Dex. In brief, NI (0.6 g, 5.3 mmol) was dissolved in DMF, to which K2CO3 (1.1 g, 7.95 mmol) was added. 6-(Boc-amino)hexyl bromide (1.56 g, 5.57 mmol) in DMF was then added dropwise and stirred at room temperature (RT) overnight. The reaction mixture was filtered and washed with methanol, after which the residual solvent was evaporated. The solid obtained was suspended in water and extracted with ethyl acetate. The organic layer was separated, dried over sodium sulfate, and concentrated to obtain the product for step 1. The resulting product was dissolved in methanol and cooled to 0 0° C., to which 10 ml of 1.25M HCl in methanol was added and stirred at RT for 24 h. The solvent was removed from the reaction mixture using the rotary evaporator. The crude solid was recrystallized from ethanol to obtain amine-functionalized 2-nitroimidazole (NI derivative).

2) Syntheses of Hypoxia-Responsive Conjugates

The NI derivative was conjugated to CM-Dex in the presence of EDC and NHS. In brief, CM-Dex (0.2 g, 0.9 mmol) was dissolved in 1:1 mixture of formamide and dimethyl formamide, after which EDC and NHS were added and stirred for 15 min. The NI derivative in DMF was slowly added to the reaction mixture and stirred for one day. An experiment was performed under a total of four conditions while changing the amounts of the NI derivative, EDC and NHS, and the conditions of the experiment are shown in Table 1 below.

TABLE 1

| Samples | NI | EDC | NHS |
|---|---|---|---|
| HR-NP1 | 0.038 g (0.18 mmol) | 0.138 g (0.71 mmol) | 0.082 g (0.71 mmol) |
| HR-NP3 | 0.076 g (0.36 mmol) | 0.276 g (1.43 mmol) | 0.162 g (1.43 mmol) |
| HR-NP8 | 0.191 g (0.9 mmol) | 0.690 g (3.6 mmol) | 0.410 g (3.6 mmol) |
| HR-NP11 | 0.382 g (1.8 mmol) | 1.380 g (7.2 mmol) | 0.830 g (7.2 mmol) |

The resulting solution was dialyzed against the excess amount of water/methanol (1 v/3 v–1 v/1 v) for 1 day and distilled water for 2 days, followed by lyophilization. The amount of the NI derivative to CM-Dex was spectrophotometrically determined from the characteristic peak of the NI derivative at 325 nm by using the UV/VIS spectrophotometer (Optizen 3220UV, Mecasys Co., Ltd., Daejeon, Korea).

Figure 1A:
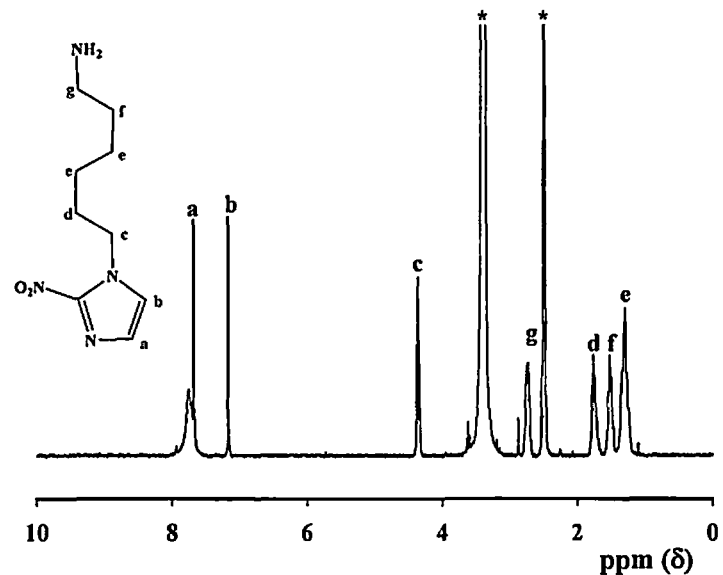
FIG. 1a shows $^1$H NMR spectra of the compound of formula 2 and its intermediate (6-(2-nitroimidazole)hexylamine).
Figure 1A:
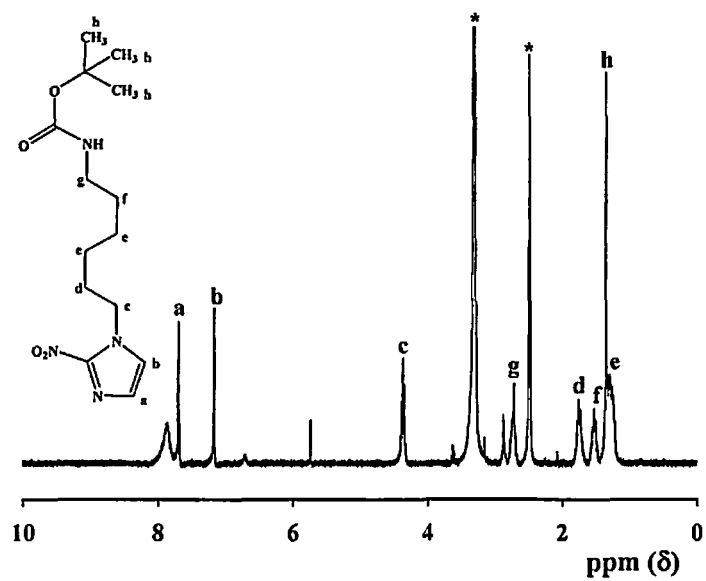

The detailed synthetic procedure to prepare the NI derivative, called (6-(2-nitroimidazole)hexylamine), and $^1$H NMR spectra demonstrating the chemical structure are shown in FIG. 1a. The chemical structure of the conjugate was characterized using $^1$H NMR (JNM-AL300, JEOL, Tokyo, Japan) operating at 300 MHz, for which the samples were dissolved in $CD_3OD$, $D_2O$ or DMSO-$D_6$.

Figure 1B:
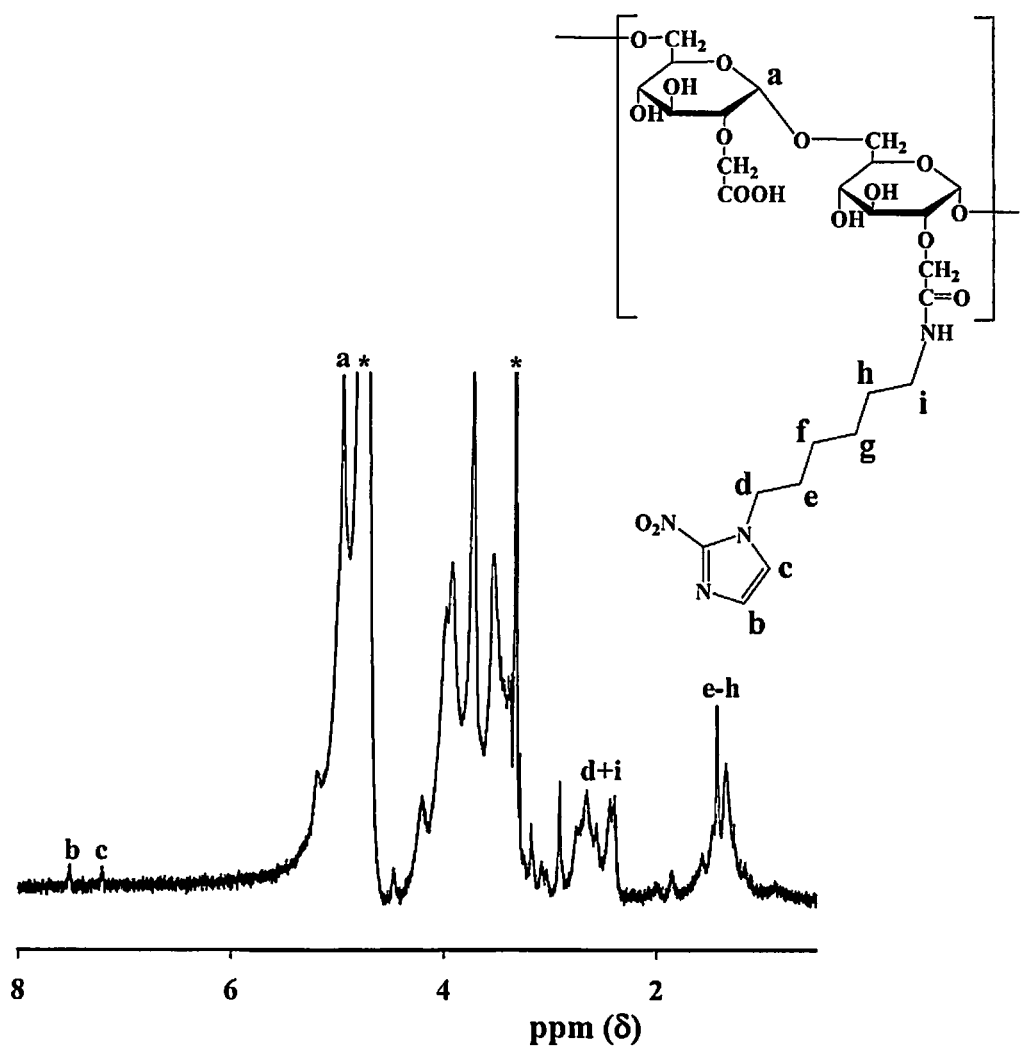
FIG. 1b shows $^1$H NMR spectra of the conjugate of the carboxymethyl dextran and the compound of formula 2 (nanoparticle).

The chemical structure of the conjugate (HR-NP11) was also confirmed using the $^1$H NMR (see FIG. 1b), in which the sample was prepared in a mixture of $D_2O$:$CD_3OD$ (1v:1v) to dissolve both the NI derivative and CM-Dex. The characteristics proton peaks of CM-Dex and the proton peaks of NI derivatives including 1.2-2.6 ppm (aliphatic protons), 7.2 and 7.4 ppm (protons of 2-nitroimidazole) were observed.

Experimental Example 1

Characterization

During synthetic procedure, the degree of substitution (DS), defined as the number of the NI derivative per 100 sugar residues of CM-Dex, was controlled by varying the molar feed ratio of the primary amino group in the NI derivative to the carboxyl group in CM-Dex. As expected, the DS increased as the feed ratio increased (Table 2). The conjugates prepared were coded depending on the DS of the NI derivative. For example, HR-NP8 indicates the conjugate with the DS value of 8. The sizes of the particles were determined at 25° C. using a FPAR-1000 fiber optics particle analyzer (Otsuka Electronics, Osaka, Japan).

From the size measurement, it was demonstrated that the self-assembled nanoparticles were constructed for the conjugate with the DS value higher than 7. The conjugate with lower DS values did not form nanoparticles, which might be due to their hydrophilicity. The mean diameters of the HR-NPs were in the range of 179-194 nm, depending on the DS value.

TABLE 2

| Samples[a] | FR[b] | DS[c] | Size (nm)[d] | X[e] |
|---|---|---|---|---|
| HR-NP1 | 0.2 | 1.86 | — | 1.65 |
| HR-NP5 | 0.4 | 3.35 | — | 2.98 |
| HR-NP8 | 1.0 | 7.99 | 176.38 ± 3.55 | 7.11 |
| HR-NP11 | 2.0 | 11.76 | 192.22 ± 3.42 | 10.47 |

[a]HR-NPs with different degree of DS values.
[b]Molar feed ratio of NI-amine to sugar residues of CM-Dex.
[c]Degree of substitution of NI-amine in a CM-Dex molecule were determined using UV-vis spectra at 325 nm.
[d]Mean diameter measured using the particle analyzer.
[e]Weight percentage of the NI derivative in the conjugate.

The morphology of the particles was observed using a TEM (TEM, Philips CM30), operated at an accelerating voltage of 200 ekV. For TEM images, samples (HR-NP8 and HR-NP11) were dispersed in distilled water and dropped on the 200 mesh copper grid. All samples were treated with 1% uranyl acetate for negative staining.

Figure 2A:
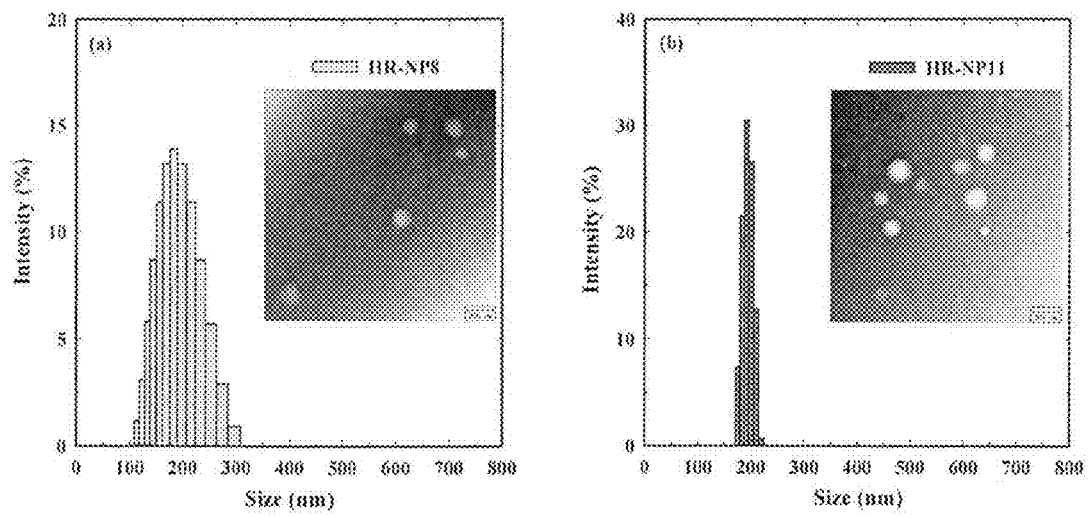
FIG. 2a shows size distribution of HR-NPs (HR-NP8 and HR-NP11) and the TEM images.
Figure 2B:
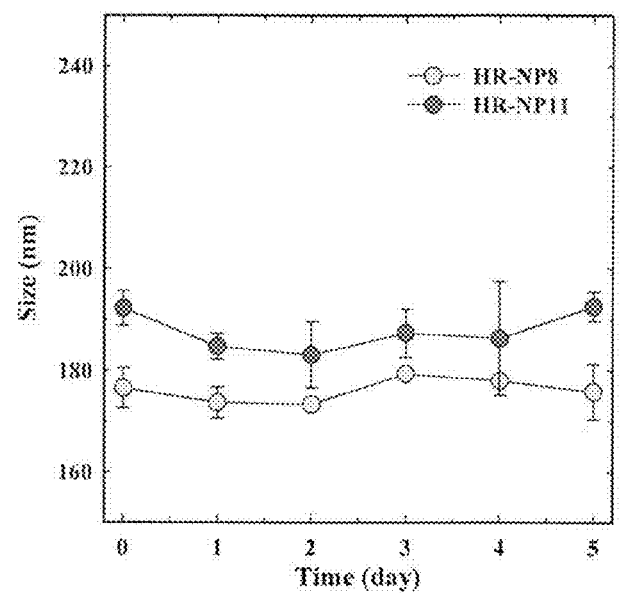
FIG. 2b shows stability of the HR-NPs (HR-NP8 and HR-NP11) in PBS (pH 7.4) as a function of time.

The TEM image demonstrated that the nanoparticles were spherical in shape (see FIG. 2a). The particle sizes of HR-NPs (HR-NP8 and HR-NP11) were preserved for at least 4 days under the physiological solution (pH 7.4) (see FIG. 2b), suggesting high stability of the nanoparticles.

The zeta potential (ζ) was measured using a zetasizer (90 PLUS, BrookHAVEN Instruments Cooperation, New York, USA). The hypoxic condition was maintained by using $CO_2$/$O_2$ incubator (Vision Scientific Co., Ltd, Korea).

The zeta potentials of all the HR-NPs (HR-NP8 and HR-NP11) were negative, indicating that nanoparticlar surfaces were covered by hydrophilic CM-Dex. Since the NI derivative was conjugated to the carboxyl group of CM-Dex, HR-NP11 exhibited the lower zeta potential value than HR-NP8 (see FIG. 3).

Experimental Example 2

The Sensitivity to Hypoxia of the HR-NPs

Figure 4:
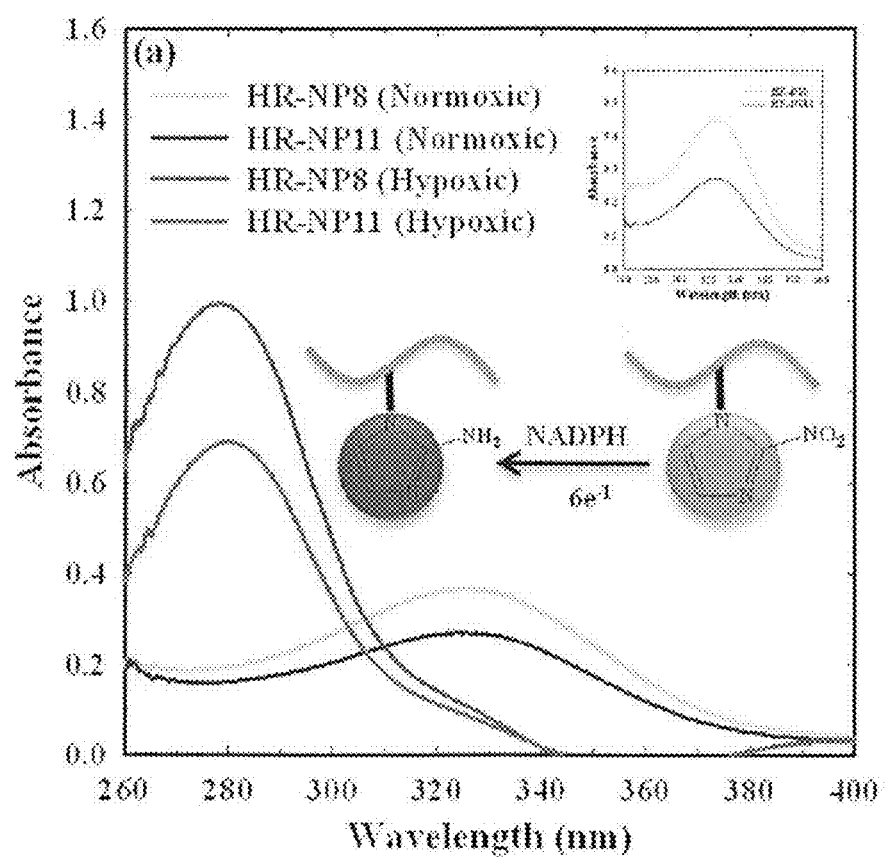
FIG. 4 shows absorption spectra of HR-NPs (HR-NP8 and HR-NP11) incubated under hypoxic and normoxic conditions for 3 h.

The sensitivity to hypoxia of the HR-NPs (HR-NP8 and HR-NP11) were assessed by measuring the change in the absorption peaks after their incubation in the normoxic (20% $O_2$, 5% $CO_2$) or the hypoxic (0.1% $O_2$, 5% $CO_2$) condition of the PBS (pH 7.4) for 3 h at 37° C. (FIG. 4). For all the HR-NPs, no significant changes of the absorption peaks were observed under the normoxic condition. Interestingly, under the hypoxic condition, the characteristic peak of 2-nitroimidazole in the conjugate at 325 nm completely disappeared, whereas the new peak appeared at 278 nm, corresponding to the characteristic peak of 2-aminoimidazole. This is consistent with the previous results showing that the nitro group of 2-nitroimidazole is converted to the amino group under the low oxygen condition. This classical reduction of nitro to amine occurs via the transfer process of six electrons, involving the nitroso (—N═O) and hydroxylamino (—NHOH) intermediates.

Figure 3:
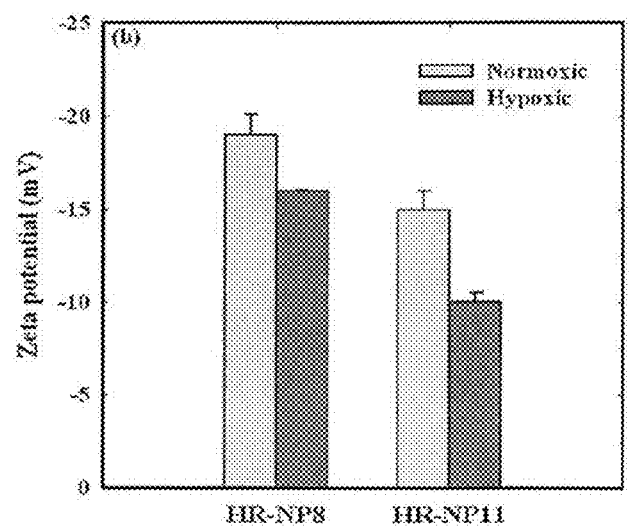
FIG. 3 shows zeta potential of the HR-NPs (HR-NP8 and HR-NP11) incubated under hypoxic and normoxic conditions with 100 M NADPH as an electron donor.

The structural change in the conjugate was further confirmed by measuring their zeta potentials. As shown in FIG. 3, no significant changes in the zeta potentials were observed when HR-NPs were incubated under the normoxic condition. However, the zeta potentials of HR-NPs significantly decreased under the hypoxic condition, owing to the presence of positively charged amino groups. In particular, the extent of the decrease in the zeta potential was much higher for HR-NP11, which was due to the larger amount of the NI derivative in the conjugate. These results indicated that HR-NPs were sensitive to hypoxia. It should be emphasized that these structural changes under hypoxia may affect the hydrophilicity of HR-NPs because the primary amino group in the conjugate is relatively hydrophilic. Indeed, 2-nitroimidazole is poorly soluble in water, whereas 2-aminoimidazole as its reductive derivative is highly water-soluble. This characteristic of 2-aminoimidazole would make the HR-NPs attractive as the drug carrier which can selectively release the hydrophobic drugs in the hypoxic condition.

Experimental Example 3

Drug Loading and Release of DOX from HR-NPs

In order to evaluate the effect of hypoxia on the drug release behavior, DOX was encapsulated into HR-NP11 as the representative sample via the emulsion method, by which the drug loading efficiency was 76%. DOX was loaded into the nanoparticles by the emulsion method. In brief, DOX.HCl (3 mg) was dissolved in chloroform containing 3.0 equimolar amount of triethylamine. The resulting solution was added to the aqueous solution containing HR-NPs (30 mg), leading to formation of an oil-in-water emulsion. This emulsion was kept in dark conditions overnight with stirring to allow evaporation of the chloroform. The solution was then dialyzed against an excess amount of distilled water for 24 h to remove unloaded DOX, followed by lyophilization to obtain DOX-HR-NPs. The loading efficiency and content of DOX in the DOX-HR-NPs were determined using a UV-vis spectrophotometer (Optizen 3220UV, Mecasys Co., Ltd., Daejeon, Korea) at 485 nm. For this experiment, DOX-HR-NPs were dissolved in a DMSO/water (1v/1v) mixture, and the calibration curve was obtained using DMSO/water (1v/1v) solutions with different DOX concentrations. The loading efficiency and loading content of DOX were calculated using the following formulas:

Loading efficiency (%)=(weight of loaded drug/ weight of drug in feed)×100%

Loading content (%)=(weight of loaded drug/weight of polymer)×100%

The loading efficiency and content of DOX into the DOX-HR-NPs was found to be 76% and 7.6 wt %, respectively.

For the release experiment, DOX-HR-NP11 was dispersed in a PBS (pH 7.4), and the solution was transferred to the cellulose membrane tubes (MWCO=3500 Da). Thereafter, the dialysis tube was immersed in a degassed PBS (pH 7.4) with 100 M NADPH and the degassing with nitrogene was continued for the whole period of the release experiment. The degassing was performed to maintain the hypoxic condition. For the control experiment (normoxic), the sample was immersed in a PBS (pH 7.4) containing 100 M NADPH without degassing. Each sample was gently shaken at 37° C. under 100 rpm. The medium was refreshed at predetermined time intervals, and the DOX concentration was measured using the UV/VIS spectrophotometer at 485 nm.

Figure 5:
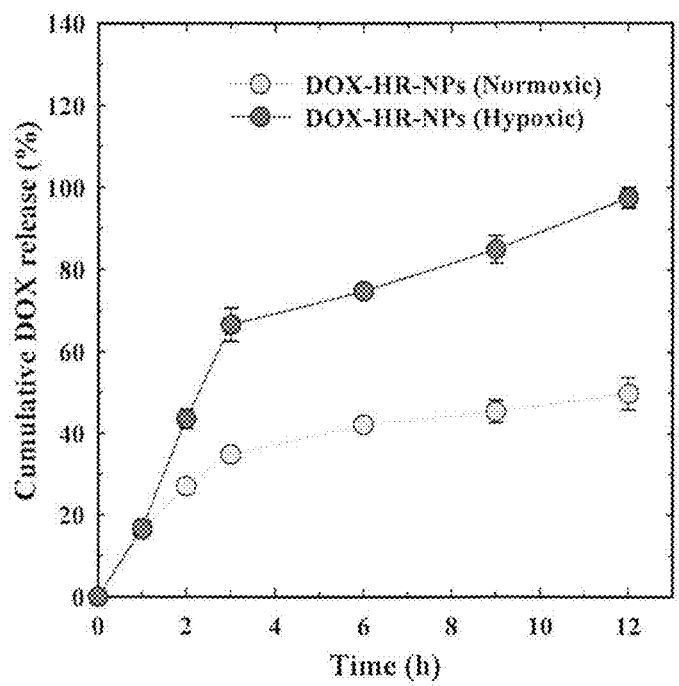
FIG. 5 shows in vitro DOX release behavior of HR-NPs under hypoxic and normoxic conditions.

DOX-loaded HR-NP11 (DOX-HR-NP11) were incubated in the hypoxic or normoxic condition for 3 h. DOX, a fluorescent drug, known to be readily encapsulated into nanoparticles in the quenched state, whereas its fluorescence is recovered upon release from the nanoparticles into the medium. Therefore, the release of DOX from HR-NP11 could be estimated by measuring its fluorescence intensity. FIG. 5 shows the representative fluorescence spectra of DOX-HR-NP11, exposed to the hypoxic and normoxic conditions for 3 h. In the normoxic condition, the fluorescence intensity of DOX slightly increased, suggesting that the minimal amount of DOX was released from HR-NP11. Of note, the strong fluorescence signal was observed when DOX-HR-NP11 were treated under the hypoxic condition, implying rapid release of DOX. The DOX release from HR-NP11 was also quantitatively analyzed as a function of time (FIG. 5). As expected, the release rate of DOX from HR-NP11 was significantly higher in the hypoxic condition than in the normoxic condition. The results exhibited that DOX was released from HR-NP11 under the normoxic condition in a sustained manner, resulting in only 49% release of DOX for 12 h. Of note, under the hypoxic condition, DOX was completely released within 12 h. This demonstrates that HR-NPs can selectively release DOX in the hypoxic condition, primarily owing to bioreduction of the hydrophobic NI derivative to the hydrophilic one.

Experimental Example 4

Cytotoxicity and Intracellular Drug Release

Figure 6A:
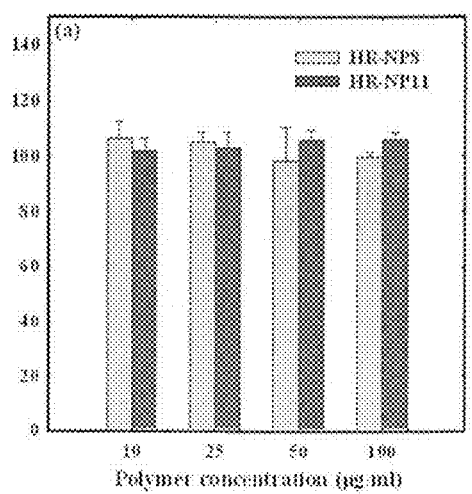
FIG. 6a shows in vitro cytotoxicities of bare HR-NPs (HR-NP8 and HR-NP11) incubated with SCC7 cells for 24 h.

To evaluate in vitro cytotoxicity of HR-NPs, they were exposed to the SCC7 cells for 24 h at 37° C., after which the cell viability was measured using the MTT assay (FIG. 6a).

SCC7 (squamous carcinoma) cell lines, obtained from the American Type Culture Collection (Rockville, Md., USA), were cultured in RPMI 1640 medium (Gibco, Grand Island, N.Y., USA) containing 10% (v/v) fetal bovine serum and 1% (w/v) penicillin-streptomycin at 37° C. in a humidified 5% $CO_2$-95% air atmosphere. The cells were seeded at a density of 1 104 cells/well in 96-well flat-bottomed plates. After one day of growth, the cells were washed twice with a PBS (pH 7.4) and incubated for 24 h with various concentrations of free DOX or DOX-HR-NPs (HR-NP8 and HR-NP11) under the hypoxic or normoxic condition. The cells were then washed twice with a PBS (pH 7.4) and the fresh culture medium was added. Twenty microliters of 3-(4,5-dimethylthiazol-2-yl)-2, 5-diphenyltetrazolium bromide solution (5 mg/ml in PBS) were added to each well, and the cells were incubated for an additional 4 h at 37° C. Subsequently, the medium was removed, and the cells were dissolved in DMSO. The absorbance at 570 nm was measured using a microplate reader (BioTek, Seoul, Korea).

Figure 6B:
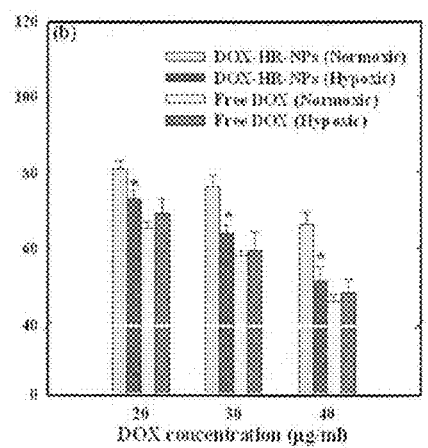
FIG. 6b shows dose dependant cytotoxicity of DOX-HR-NPs and free DOX.

Up to the polymer concentration of 100 g/ml, HR-NP8 and HR-NP11 showed no significant cytotoxicity to SCC7 cells. The cytotoxicities of DOX-HR-NP11 and free DOX were also evaluated in the normoxic and hypoxic conditions (FIG. 6b). Cytotoxicity of free DOX in the hypoxic condition was comparable to that in the normoxic condition. On the other hand, DOX-HR-NP11 in the hypoxia condition showed significantly higher cytotoxicty than those in the normoxic condition. This might be due to the rapid release of DOX from HR-NP11 under the reduced oxygen concentration, as shown in FIG. 5. Overall, these results support the hypoxia-triggered release of DOX from HR-NP11.

To investigate the intracellular drug release from the HR-NP11, the cells were incubated with DOX-HR-NP11 under the hypoxic or normoxic condition for 12 h. The cells were then washed twice with a PBS (pH 7.4) and fixed with 4% formaldehyde solution. For nuclear staining, the cells were incubated with 4,6-diamino-2-phenylinodole (DAPI) for 10 min at RT, followed by washing with a PBS (pH 7.4). The intracellular localization of DOX, released from HR-NP11, was observed using IX81-ZDC focus drift compensating microscope (Olympus, Tokyo, Japan).

Figure 7:
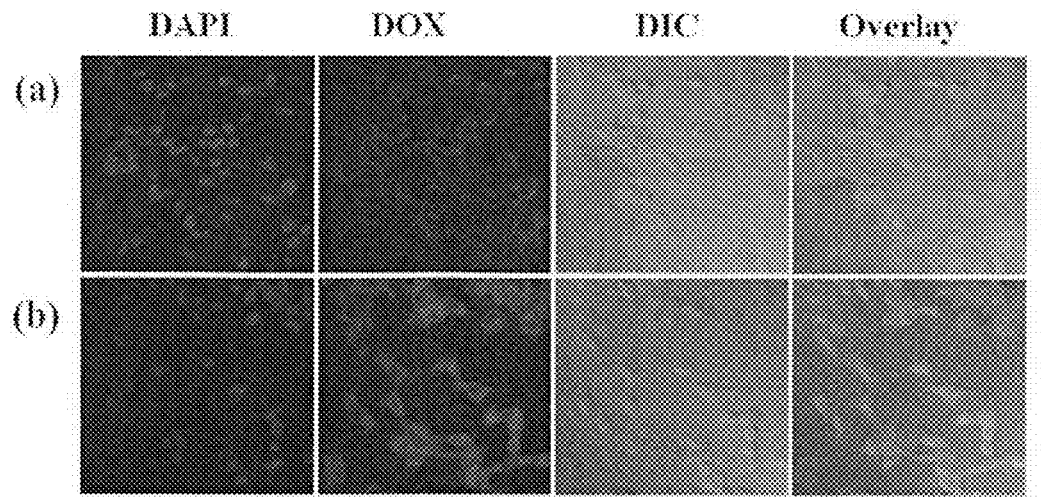
FIG. 7 shows intracellular release of DOX from the HR-NPs under (a) normoxic and (b) hypoxic conditions.

To verify intracellular drug release, the DOX-HR-NP11 were monitored using the fluorescence confocal microscopy after they were treated with the SCC7 cancer cells. The results showed that, after a 12 h incubation of DOX-HR-NP11 under the hypoxic condition, strong fluorescence was observed at the cytoplasm of the cell, indicating the rapid release of DOX from the nanoparticles (FIG. 7). On the contrary, the sample incubated under the normoxic condition showed the weak fluorescent signal at the cytoplasm of the cell. This results are in a good agreement with the in vitro release behavior (FIG. 5). Overall, it is evident that the hypoxia-sensitive DOX-HR-NP11, prepared in this study, have the ability for an effective delivery of the hydrophobic drugs into the hypoxic cells.

Experimental Example 5

In Vivo Biodistribution of HR-NPs and Tissue Staining

Although numerous nanoparticles showed excellent properties as the drug carrier in vitro, clinical applications have been often limited by undesirable biodistribution and poor tumor targetability. To evaluate tumor targetability of HR-NPs(HR-NP11), their in vivo biodistribution were assessed using a real-time near-infrared fluorescence (NIRF) imaging technique, following systemic administration of Cy5.5-labeled HR-NP11 into the tail vein of SCC7 tumor-bearing mice.

The tumor-bearing mice were prepared by injecting a suspension of $1 \times 10^6$ SCC7 cells in physiological saline (100 μl) into the subcutaneous dorsa of athymic nude mice (7 weeks old, 20-25 g). After 14 days of subcutaneous inoculation, Cy5.5-HR-NP11 were injected into the tail vein of the tumor-bearing mice at a dose of 5 mg/kg. The biodistribution of HR-NP11 were evaluated as a function time using explore Optix system (ART Advanced Research Technologies Inc., Montreal, Canada). Laser power and count time settings were optimized at 15 μW and 0.3 s per point. Excitation and emission spots were raster-scanned in 1 mm steps over the selected region of interest. A 670 nm-pulsed laser diode was used to excite the Cy5.5 molecules. The fluorescence emission at 700 nm was collected and detected through the fast photomultiplier tube (Hammamatsu, Japan) and a time-correlated single photon counting system (Becker and Hickl Gmbh, Berlin, Germany), respectively. The major organs and tumors were dissected from SCC7 tumor-bearing mice at 24 h after intravenous injection of Cy5.5-HR-NP11. NIR fluorescence images of dissected organs and tumors were obtained with a 12-bit CCD camera (Kodak Image Station 4000 MM, New Haven, Conn.) equipped with a special C-mount lens and Cy5.5 bandpass emission filter (680 nm to 720 nm; Omega Optical). The tissue distribution of HR-NP11 was quantified by measuring the NIR fluorescence intensity at the region of interest. All values are expressed as means±SD for groups of five animals.

For hypoxic tissue staining, pimonidazole.hydrochloride (Hypoxyprobe™-1) as a hypoxic staining probe was used. Pimonidazole is activated in hypoxic cells and subsequently form covalent adduct with thiol-containing proteins, peptides and amino acids. The adduct can be stained using fluorecently labelled monoclonal antibody (Mabl). Pimonidazole.hydrochloride (100 mg/kg) was intravenously administered into the tail vein of SCC7 tumor-bearing mice, thirty minutes later Cy5.5-HR-NP11 (5 mg/kg) was injected and allowed for 1 hr. Finally, Hoechst 33342 was injected and allowed for 10 min to label cell nuclei. For hypoxic tissue staining, tumor tissues were removed from the sacrificed mice, fixed with 2% paraformaldehyde solution, and embedded in paraffin. Frozen tissues were sectionalized from 10 to 20 μm using a Cryostat Microtome (CM1850, Leica Microsystems Nussloch GmbH, Germany). Frozen sections were transferred to 4% paraformaldehyde for fixation at 4° C. for 20 minutes. Fixed slides were washed in PBS and incubated with methanol at −20° C. for 10 minutes, and blocked with PBS containing 1% bovine serum albumin. Pimanidazole adducts were detected with FITC-conjugated IgG1 mouse monoclonal antibodies (clone 4.3.11.3, Hypoxyprobe, Inc. Burlington, Mass., USA) at 1:400 dilution for 1 h. Finally, the stained sections were added with mounting solution, covered with a cover slip, and analyzed with a confocal microscope (LSM 700, Carl Zeiss Micro Imaging GmbH, Germany) equipped with a 40× water-emersion objective.

Figure 8A:
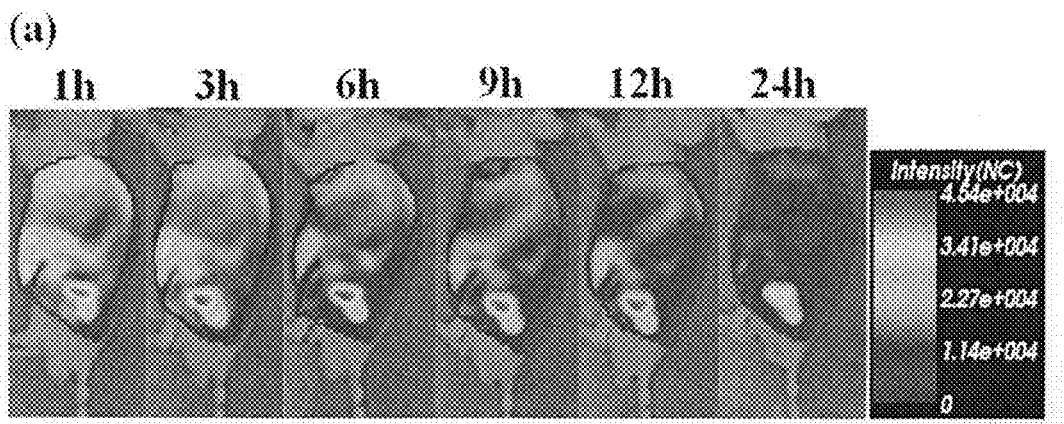
FIG. 8 shows in vivo non-invasive fluorescence imaging of HR-NP11 in tumor-bearing mice. (a) Time-dependant whole body image of athymic nude mice bearing SCC7 tumors after intravenous injection of Cy5.5-HR-NP11, (b) ex vivo fluorescence image of normal organs and tumor tissues collected at one day post-injection of HR-NP11, (c) quantification of HR-NP11 in normal organs and tumor tissue. Error bars represent the standard deviation for five animals per group and (d) histological staining of hypoxic tumor tissue. FITC-labelled monoclonal antibody was used for staining hypoxic tissue.
Figure 8B:
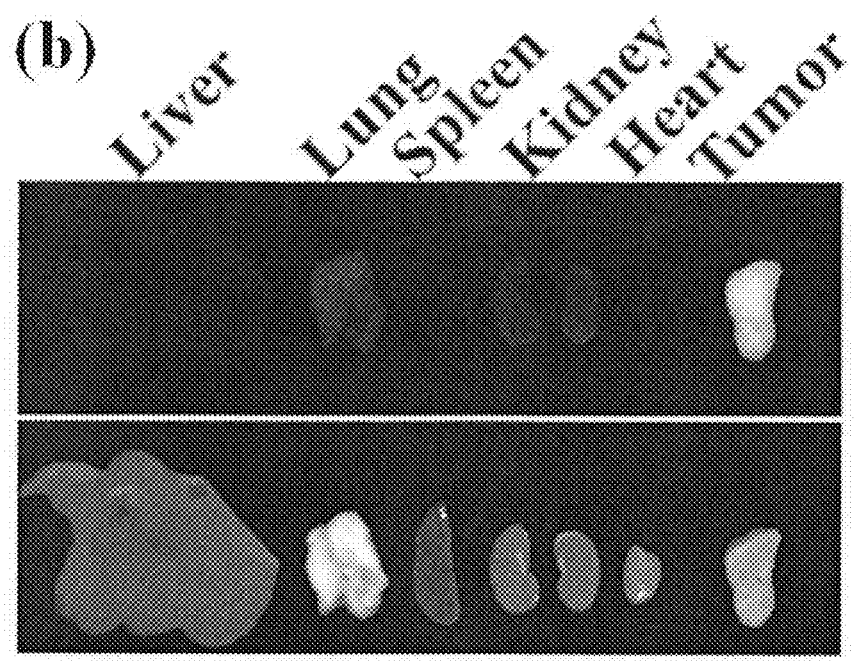
Figure 8C:
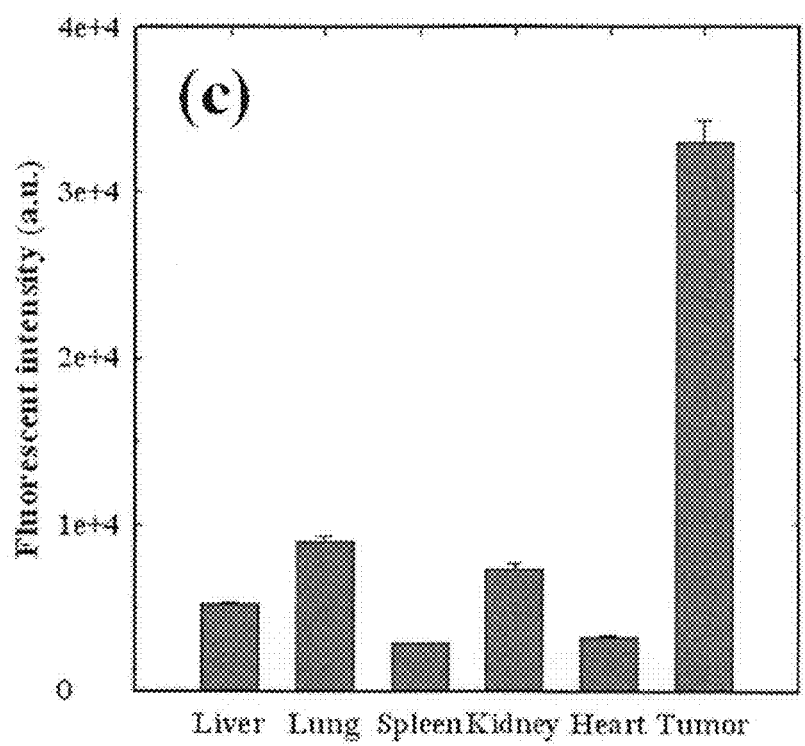
Figure 8D:
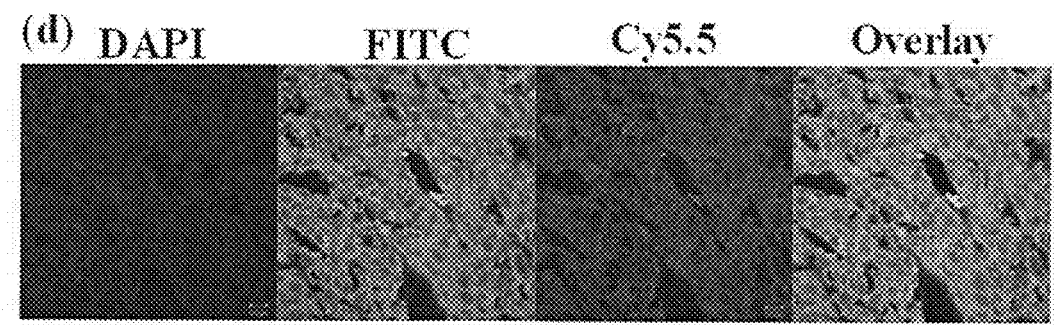

The significant NIRF signals were found in the whole body for up to 12 h, suggesting prolonged circulation of HR-NP11 in blood (FIG. 8a). Interestingly, the strong NIRF signal at the tumor site was observed only at 1 h post-injection, which was maintained for up to 12 h. The ex vivo image of the tissues, retrieved at 24 h post-injection, supported high tumor targetability of HR-NP11 (FIG. 8b). Quantitative analysis indicated that the amount of HR-NP11 at tumor tissue is at least 4-fold higher than those in normal organs including liver, lung, spleen, kidney, and heart (FIG. 8c). The nanoparticular distribution at the hypoxic tumor tissue was also observed using the immunohistochemistry technique. As shown in FIG. 8d, the hypoxic tissue, stained by the FITC-labelled monoclonal antibody, imbibed large amount of HR-NP11. These results suggest that HR-NPs can effectively reach the hypoxic tumor site after systemic administration in vivo.

Experimental Example 6

In Vivo Antitumor Efficacy of DOX-HR-NPs

To evaluate the anti-tumor efficacy of HR-NPs, SCC7 tumor bearing mice were prepared, as previously described. Mice were divided into three groups: (i) normal saline (ii) free DOX at 5 mg/kg, and (iii) DOX-HR-NP11 at 5 mg DOX/kg. When tumors reached 8 mm in diameter, each sample was injected once every three days. Tumor volumes were calculated as $a \times b^2/2$, were a was the largest and b the smallest diameter. The statistical significance of differences (p<0.05) between groups tested was determined using one-way ANOVA test.

Figure 9A:
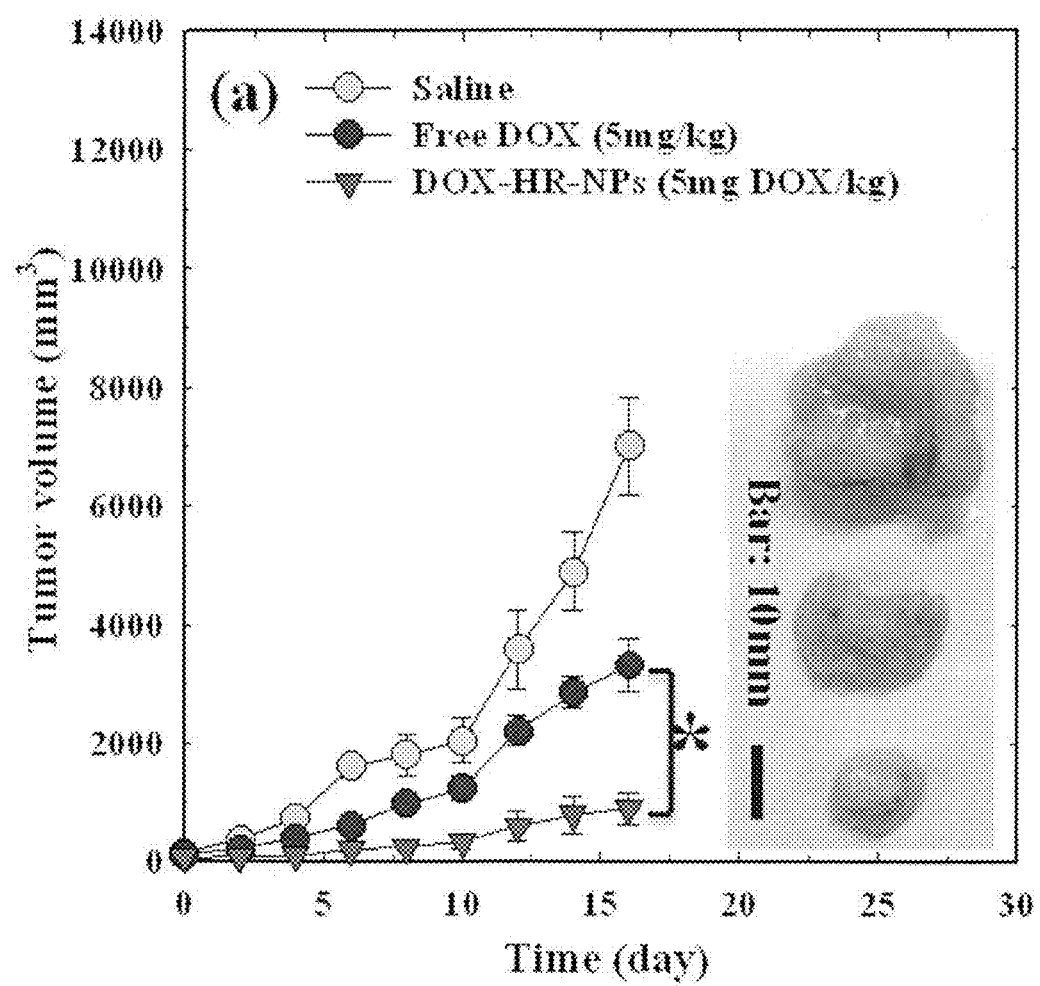
FIG. 9 shows antitumor efficacy of DOX-HR-NP11. (a) Tumor growth of SCC7 cancer xenografts treated with saline, free DOX, and DOX-HR-NP11 at a DOX dose of 5 mg/kg. Insets are the representative tumor images excised at 16 days post-treatment, (b) tumor weights at 16 days post-treatment. Error bars represent standard deviation for five animals per group. Asterisks (*) denote statistically significant differences ($p<0.05$) calculated by an one-way Anova test.
Figure 10:
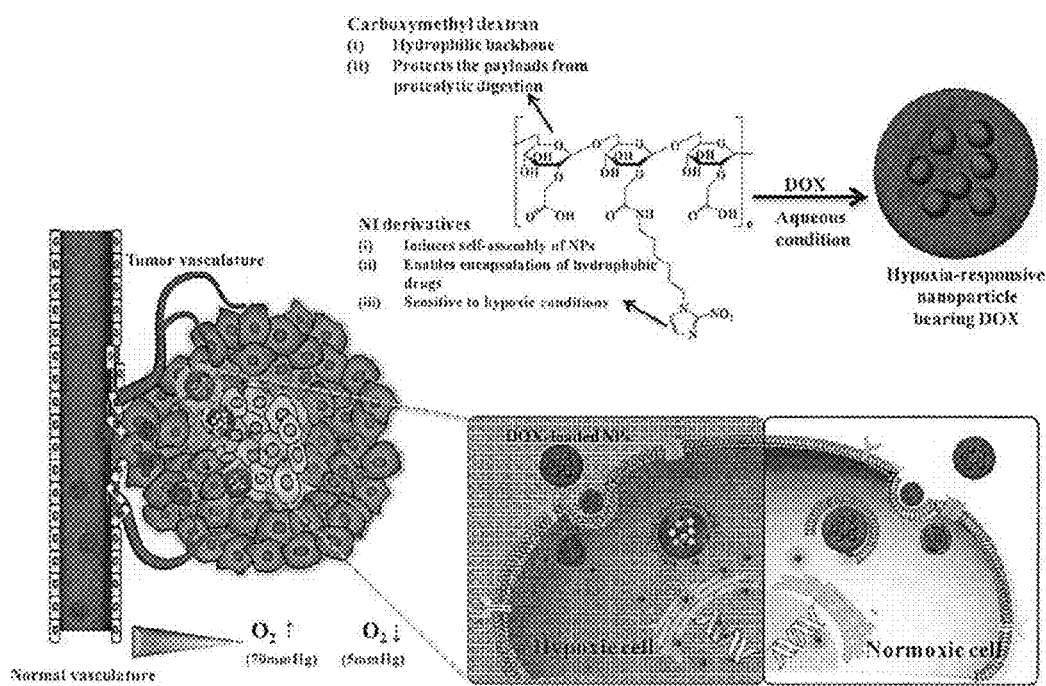
FIG. 10 shows schematic illustration of the formation of drug-loaded HR-NPs nanoparticles and in vivo tumor-targeting pathways. The HR-NPs can reach the tumor site via the EPR effect, followed by intracellular drug release at hypoxic tissue.

The control group, treated with saline, exhibited a rapid increase in the tumor volume as a function of time. Free DOX also showed the considerable increase in the size, which is due to lack of tumor targetability. Notably, minimal increase in the tumor volume was found for the group treated with DOX-HR-NP11, suggesting the high antitumor efficacy (FIG. 9a). As expected, the mice treated with DOX-HR-NP11 had the lowest weight among the groups (FIG. 9b). This high antitumor activity of DOX-HR-NPs might be due to their selective accumulation in tumor, followed by the intracellular release at the hypoxic cells (FIG. 6).

In summary, live animal NIRF imaging demonstrated that HR-NPs could effectively accumulate at the tumor site. As a consequence, DOX-HR-NPs exhibited enhanced antitumor efficacy, compared to free DOX. Overall, the results indicated that HR-NPs are promising drug carriers for selective delivery of hydrophobic drugs into hypoxic cells.

The invention claimed is:
1. An amphiphilic polymer wherein a compound of the following formula 1, which has an amine group, is conjugated by an amide bond to a carboxymethyl dextran (CM-Dex) having a carboxyl group:

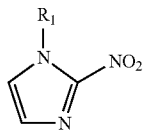

Formula 1 wherein $R_1$ is amine or a $C_1$ to $C_{10}$ alkylamine;
wherein 8-20 compounds of formula 1 are conjugated per 100 carboxyl groups of the carboxymethyl dextran.

2. The amphiphilic polymer of claim 1, wherein the polymer has a molecular weight of 5,000-1,000,000.

3. The amphiphilic polymer of claim 1, wherein the compound of formula 1 is a compound of the following formula 2:

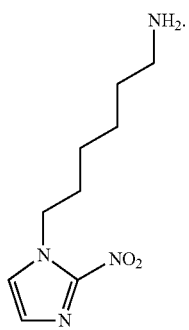

Formula 2

4. The amphiphilic polymer of claim 1, wherein the carboxymethyl dextran forms a hydrophilic backbone, and the compound of formula 1 is conjugated by the amide bond to the carboxymethyl dextran to impart hydrophobicity, and thus the resultant polymer has amphiphilicity.

5. The amphiphilic polymer of claim 1, wherein 8-11 compounds of formula 1 are conjugated per 100 carboxyl groups of the carboxymethyl dextran.

6. Nanoparticles formed by self-assembly of the amphiphilic polymer of claim 1 in an aqueous solvent, wherein 8-20 compounds of formula 1 are conjugated per 100 carboxyl groups of the carboxymethyl dextran,
wherein the compound of formula 1 is located in the core of the nanoparticle, and a carboxymethyl dextran is located in the shell of the nanoparticle.

7. The nanoparticles of claim 6, wherein a nitro group in the compound of formula 1 in the nanoparticle is reduced to an amino group under an oxygen partial pressure of 20 mmHg or lower.

8. The nanoparticles of claim 6, wherein the nanoparticles have an average diameter of 170 nm to 500 nm.

9. The nanoparticles of claim 6, wherein the nanoparticles have an average diameter of 170 nm to 200 nm.

10. The nanoparticles of claim 6, wherein the nanoparticles include a hydrophobic additive encapsulated therein.

11. The nanoparticles of claim 10, wherein the additive is any one or more drugs selected from the group consisting of paclitaxel, doxorubicin, cis-platin, decetaxel, tamoxifen, camtothecin, anasterozole, carboplatin, topotecan, belotecan, irinotecan, gleevec, vincristine, salicylates, ibuprofen, naproxen, fenoprofen, indomethacin, phenyltazone, methotrexate, cyclophosphamide, mechlorethamine, dexamethasone, prednisolone, celecoxib, valdecoxib, nimesulide, cortisone and corticosteroid.

12. The nanoparticles of claim 10, wherein a nitro group in the compound of formula 1 in the nanoparticles is reduced to an amino group under an oxygen partial pressure of 20 mmHg or lower so that the compound is made hydrophilic and the hydrophobic additive is released.

13. The nanoparticles of claim 6, wherein the amphiphilic polymer has a molecular weight of 5,000-1,000,000.

14. The nanoparticles of claim 6, wherein the compound of formula 1 is a compound of the following formula 2:

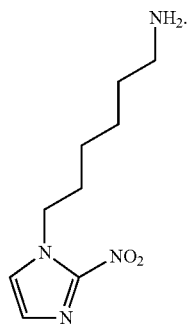

Formula 2

15. The nanoparticles of claim 6, wherein the carboxymethyl dextran forms a hydrophilic backbone, and the compound of formula 1 is conjugated by the amide bond to the carboxymethyl dextran to impart hydrophobicity, and thus the polymer has amphiphilicity.

16. The nanoparticles of claim 6, wherein 8-11 compounds of formula 1 are conjugated per 100 carboxyl groups of the carboxymethyl dextran.

* * * * *